United States Patent [19]

Russell

[11] 3,941,927

[45] Mar. 2, 1976

[54] OPTICAL FIBER DEFLECTION DEVICE

[75] Inventor: James T. Russell, Richland, Wash.

[73] Assignee: Battelle Development Corporation, Columbus, Ohio

[22] Filed: Nov. 11, 1974

[21] Appl. No.: 522,702

[52] U.S. Cl. ............ 178/7.6; 178/DIG. 2; 340/108; 350/96 R
[51] Int. Cl.[2].. G02B 5/14; G01D 5/26; H04N 1/04; H04N 3/04
[58] Field of Search . 178/7.6, 7.1, DIG. 2, DIG. 27; 346/108, 109; 350/6, 96 R, 96 B, 285

[56] References Cited
UNITED STATES PATENTS

| | | | |
|---|---|---|---|
| 2,920,529 | 1/1960 | Blythe | 346/109 |
| 3,029,318 | 4/1962 | Fay | 360/107 |
| 3,112,360 | 11/1963 | Gregg | 178/7.6 |
| 3,437,393 | 4/1969 | Baker | 178/7.6 |
| 3,470,320 | 9/1969 | Pike | 178/7.6 |
| 3,471,641 | 10/1969 | Baker | 178/7.6 |
| 3,530,258 | 9/1970 | Gregg | 179/100.3 |
| 3,541,442 | 11/1970 | Gaston | 178/7.6 |
| 3,836,225 | 9/1974 | Wilde | 178/7.6 |

OTHER PUBLICATIONS
Uchida et al., "IEEE Journal of Quantam Electronics," Vol. QE-6, No. 10, Oct. 1970, pp. 606–612.

*Primary Examiner*—Howard W. Britton
*Attorney, Agent, or Firm*—Klarquist, Sparkman, Campbell, Leigh, Hall, & Whinston

[57] ABSTRACT

An optical fiber deflection device is described in which an electrical transducer is used for deflecting the fiber in response to an electrical control signal in order to deflect a light beam transmitted through such fiber. The transducer includes a nonmagnetic deflector means attached to the fiber and connected to an electrical current source, for deflection of the fiber by movement of the deflector means. In one embodiment employing an electromagnetic transducer, an electrical conductor is attached along the length of the fiber and is connected to a D.C. current source to produce a magnetic field around the conductor so that they may be deflected by pairs of electromagnetic coils positioned adjacent the side of the conductor when a control signal is applied to such coils. Alternatively, the control signal can be applied to the conductor attached to the optical fiber and a D.C. current caused to flow through the electromagnetic coils. Other embodiments of the invention use a piezoelectric transducer means including a piezoelectric element attached to the optical fiber so that they are deflected in response to a control signal applied to such element. In still another embodiment of the invention, the electromagnetic transducer means includes electromagnetic coils provided around a pair of magnetostrictive wires each having one end fixed and their other ends attached to the fiber, so that such wires expand and contract to deflect the fiber when a control signal is applied to such coils. In a further embodiment, a thermoelectric transducer means is used including a thermal expansion element, such as a bimetal strip, attached to the fiber and an electrical heating element supported adjacent to such expansion member so that when a control signal is applied to such heating element, the expansion member bends an amount corresponding to the current of such signal to deflect the fiber.

14 Claims, 8 Drawing Figures

U.S. Patent March 2, 1976 3,941,927
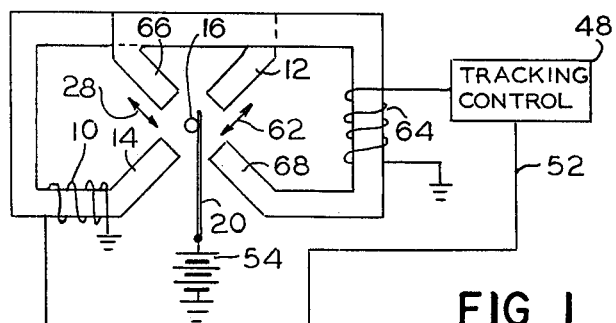
FIG. 2
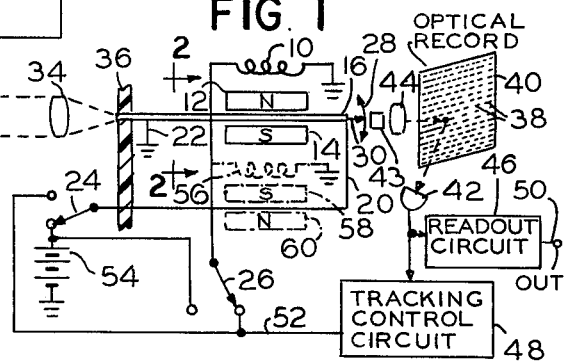
FIG. 1
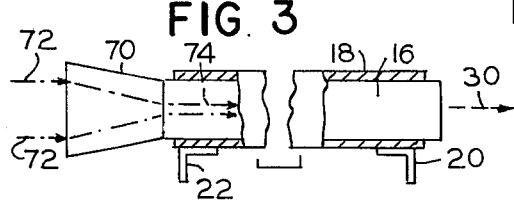
FIG. 3
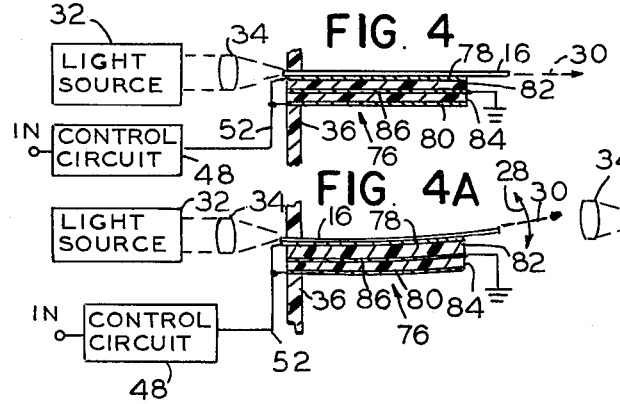
FIG. 4
FIG. 4A
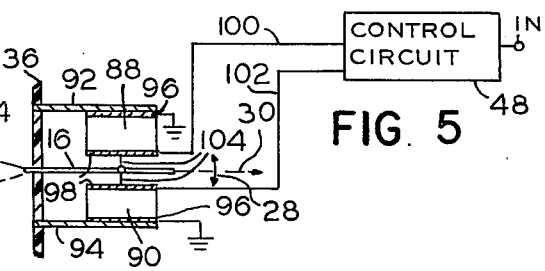
FIG. 5
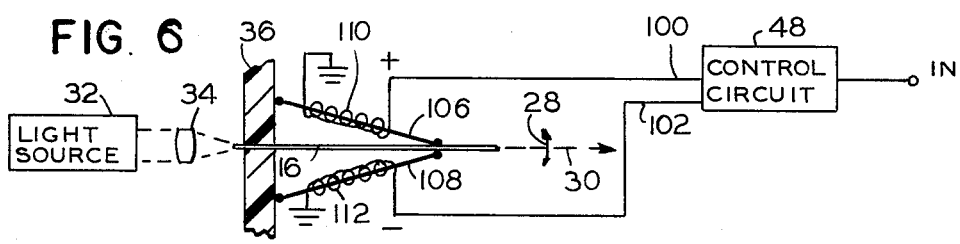
FIG. 6
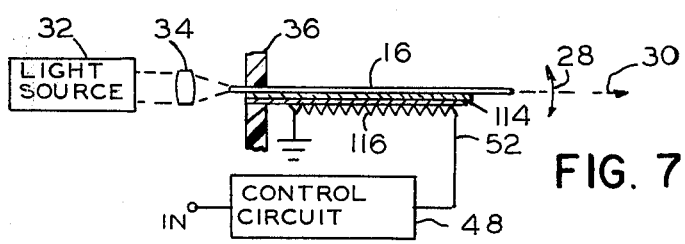
FIG. 7

OPTICAL FIBER DEFLECTION DEVICE

BACKGROUND OF THE INVENTION

The subject matter of the present invention relates generally to light beam deflection apparatus employing an optical fiber which is deflected by a transducer in response to an electrical control signal, and in particular to such an apparatus in which the transducer includes a deflection means attached to the optical fiber and connected to a source of electrical current for deflection of the fiber by movement of such deflection means. The optical fiber deflection device of the present invention is especially useful for scanning optical records of high density data recorded in tracks of data spots representing digital information, as shown in U.S. Pat. No. 3,501,586 of Russell, granted Mar. 17, 1970, or analog information such as the pulse length or frequency modulated data spots of U.S. Pat. No. 3,530,258 of Gregg et al, granted Sept. 22, 1970.

Previously it has been proposed in U.S Pat. No. 3,470,320 of Pike et al, granted Sept. 30, 1969, to provide a light scanner including an optical fiber which is deflected electrostatically or electromagnetically. Electromagnetic deflection apparatus has an advantage over electrostatic deflection apparatus since it is of lower impedance which is more suitable for the transistors used to drive the deflection circuits. However, in the electromagnetic deflection apparatus of Pike, a metal armature of iron or other magnetic material is attached to the glass fiber to enable such fiber to be deflected by electromagnets whose coils are connected to the sources of the deflection signals. This has the disadvantage that the mass which must be moved in order to deflect the fiber is greatly increased, thereby reducing the maximum frequency response and increasing the signal amplitude which must drive the electromagnets. A similar problem is created by the optical fiber deflection apparatus shown in the above-mentioned U.S. Pat. No. 2,530,258 which employs an optical fiber mounted on a strip of magnetic material which greatly increases the mass that is deflected.

The above-mentioned problems are overcome by the optical fiber deflection device of the present invention. In the preferred embodiment of the electromagnetic deflection apparatus of the invention, a romagnetic deflector means formed by a thin wire or conductive layer, is attached to the surface of the fiber and electrical current is caused to flow through such wire or conductive layer to produce a magnetic field around the fiber. The surrounding magnetic field enables the optical fiber to be deflected by an electromagnet or other electromagnetic transducer means in accordance with a control signal applied thereto. As a result of the decrease in mass of the deflected fiber and the conductive element attached thereto, the deflection device of the present invention is capable of operating at a greater frequency and consumes less power than that of the prior art. In addition, other embodiments of the present invention are described using different transducer means for deflecting the optical fiber.

When the optical fiber is employed to scan the light beam along the data track of an optical record, the deflection device of the present invention may be used for tracking purposes to deflect such beam laterally with respect to the center of the track in order to maintain such beam on the track at all times. Such a tracking means is much less expensive and has a faster response than conventional mechanical tracking and those employing rotating mirrors or other moving optical elements. Furthermore, the optical system can be simplified when using an optical fiber of the self-focusing type, such as that described by Uchida et al in "IEEE Journal of Quantam Electronics," Vol. QE-6, No. 10, October 1970, pages 606 to 612. Since the index of refraction of the glass in a self-focusing fiber decreases with increasing distance from its center, such fiber focuses the input light beam to a small focal point at its output. The self-focusing fiber may be provided with a conical input end which focuses the light rays to a narrow beam within the fiber so that a converging lens need not be employed between the input end of the optical fiber and the light source. In addition to the tracking deflection transverse to the data track, a second deflection motion parallel to the data track can be provided by a second transducer for scanning or for correcting errors in the record, such as when the data tracks are not concentric with the scanner wheel carrying the objective lenses used for scanning. It is also possible to provide deflection in a third direction perpendicular to the record for maintaining the light beam in focus on the data track. This can be accomplished by bending the fiber to provide a fiber portion parallel to the record and deflecting such fiber portion with a third transducer.

SUMMARY OF THE INVENTION

It is, therefore, one object of the present invention to provide an improved light beam deflection apparatus of simple and inexpensive construction, including an optical fiber which is deflected by an electrical transducer having a current conducting element attached to the fiber.

Another object of the invention is to provide such an optical fiber deflection device in which an electrical transducer includes a nonmagnetic deflector means attached to the optical fiber which deflects the fiber in response to an electrical control signal in a fast and efficient manner.

A further object of the invention is to provide such an optical fiber deflection device employing an electromagnetic transducer in which electric current is transmitted through a conductor attached to the optical fiber in order to create a magnetic field around the fiber so that it may be deflected electromagnetically.

An additional object of the invention is to provide such an optical fiber deflection apparatus in which the transducer is an electromagnetic transducer of low impedance so that it may be driven with a control signal current of relatively low voltage.

Still another object of the present invention is to provide such an optical fiber deflecting means in which the fiber is deflected by a piezoelectric transducer including a piezoelectric element attached to the fiber.

A still further object of the invention is to provide such an optical fiber deflection device in which the electromagnetic transducer includes magnetostrictive wire attached to the fiber at one end and fixed at its other end so that it deflects such fiber when a control signal is transmitted through electromagnetic coils surrounding such wire.

A further object of the present invention is to provide such an optical fiber deflection device in a tracking apparatus for scanning a light beam along the data track on an optical record.

BRIEF DESCRIPTION OF DRAWINGS

Other objects and advantages of the present invention will be apparent from the following detailed description of certain preferred embodiments thereof, of which:

FIG. 1 is a schematic diagram showing a preferred embodiment of the optical fiber deflection apparatus of the present invention used for tracking data tracks on an optical record;

FIG. 2 is a schematic diagram of the apparatus of FIG. 1 taken on a vertical section view on line 2—2 of FIG. 1;

FIG. 3 is an enlarged view of the optical fiber used in FIGS. 1 and 2 with a portion of the conductor layer broken away for purposes of clarity;

FIG. 4 is a section view showing another embodiment of the optical fiber deflection device of the present invention employing a bending type of piezoelectric transducer;

FIG. 4A is a section view of the device of FIG. 4 showing the piezoelectric element and optical fiber in a bent position as a result of the application of a control signal thereto;

FIG. 5 is a schematic diagram of a third embodiment of the present invention employing piezoelectric transducer means of the expansion and contraction type.

FIG. 6 is a schematic diagram of a fourth embodiment of the present invention in which the transducer means includes magnetostrictive wires attached to the optical fiber; and FIG. 7 is a schematic diagram of a fifth embodiment of the invention in which the transducer means is a thermoelectric element which bends the thermoelectric element.

DESCRIPTION OF PREFERRED EMBODIMENTS

As shown in FIG. 1, one embodiment of the optical fiber deflection apparatus of the present invention includes an electromagnetic transducer means comprising an electromagnetic coil 10 which is coupled to a magnetic metal core whose ends form spaced pole pieces 12 and 14, which are positioned on opposite sides of an optical fiber 16. The optical fiber is made of light transparent glass or plastic and is attached to a nonmagnetic deflector means provided by a coating 18 of metal or other nonmagnetic conducting material on the surface of such fiber. The conductive coating is electrically connected at one end to a lead wire 20 and at its other end to lead wire 22, as shown in FIG. 3. One of the lead wires is grounded, while the other is connected to a source of electrical current through the movable contact 24 of an electrical switch so that current flows through the conductive coating 18 and produces a magnetic field around the optical fiber 16. This surrounding magnetic field enables such fiber to be deflected by the electromagnetic coil 10 and pole pieces 12 and 14 when a control signal is transmitted to the coil 10 through the movable switch contact 26 of a second switch. As a result, the optical fiber 16 is deflected vertically in a direction perpendicular to the field between the pole pieces, as shown by arrows 28, and a light beam 30 transmitted through such optical fiber is similarly deflected.

The light beam may be formed by a laser or other light source 32 and transmitted through a converging lens 34 which focuses such light on the input end of the optical fiber 16, such input end being held in a fixed position by a support member 36. The output end of the optical fiber 16 is free to move and is deflected by the electromagnetic transducer means described previously to cause the light beam 30 to be deflected laterally across data track lines 38 on an optical record 40 containing digital information or analog information in the form of frequency modulated or pulse length modulated data spots in such track lines. The data spots may be light opaque on a transparent background or they may be light transparent on an opaque background when a light transmission type record is employed. However, the data spots may also be light reflecting so that the light beam 30 is reflected from the spots onto a photocell or other photoelectric detector 42. Thus, the optical record is scanned by a scanning device 43 which deflects the light beam 30 longitudinally along the data track lines 38 in any suitable manner, such as by a rotating mirror as shown in U.S. Pat. No. 3,501,586 or moving a scanner wheel supporting a plurality of objective lenses 44 between the output end of the optical fibers 16 and such record in the manner shown in copending U.S. patent application Ser. No. 516,453, filed Oct. 21, 1974 of J. T. Russell, entitled MULTI-LAYERED OPTICAL DATA RECORDS AND PLAYBACK APPARATUS. Therefore, the details of this scanning apparatus will not be referred to further.

The electrical output signal of the photocell 42 is transmitted to a readout circuit 46 and to a tracking control circuit 48. The readout circuit produces an output signal at an output terminal 50 which corresponds to the data recorded in the data track lines 38 of the record 40. However, the tracking control circuit produces an output signal whose amplitude is related to the distance the light beam 30 strays from the center of the track line being scanned. One such tracking control circuit is shown in pending U.S. patent application Ser. No. 483,131 of R. A. Walker, filed June 26, 1974. The output of the tracking control circuit is transmitted through a conductor 52 to the coil 10 when switch contact 26 is in a position shown. This tracking signal causes the electromagnetic transducer to deflect the fiber 10 toward the center of the data track line being scanned and thereby causes proper tracking of the light beam 38 along such track line. In the shown positions of switch contacts 24 and 26, a D.C. current source 54 is connected by switch contact 24 through lead 20 to the conductive layer 18 on the outer surface of the optical fiber in order to transmit a D.C. current therethrough to the grounded lead 22. However, it is also possible to change the positions of switch contacts 24 and 26 so that the D.C. current source 54 is connected through contact 26 to the coil 10 of the electromagnetic transducer while the tracking signal output 52 is connected through contact 24 to the conductive layer 18 on the optical fiber. In either case, the optical fiber and light beam transmitted therethrough will be deflected vertically in the direction of arrows 28 in accordance with the tracking signal. It should be noted that in the second case, the D.C. current source 54 may be eliminated if the pole pieces 12 and 14 are replaced by permanent magnets. Also, the conductive coating 18 on the surface of the optical fiber 16 can be replaced by a thin metal wire suitably attached along the length of such fiber so that it is merely an extension of lead wires 20 and 22.

In order to increase the maximum deflection speed of the optical fiber 16 in the apparatus of FIG. 1, it may be desirable because of the added mass of the lead wire to provide a second electromagnetic transducer means for deflecting the lead wire 20 simultaneously with deflection of such fiber. Thus, a second coil 56 may be provided around a second magnetic core having pole pieces 58 and 60 on opposite sides of the lead wire, as shown in phantom lines in FIG. 1. It should be noted that the upper pole piece 58 and the bottom pole piece 60 are of opposite polarity to the upper pole piece 12 and the bottom pole piece 14 of the first mentioned transducer because the electrical current flows in opposite directions through wire 20 and conductive coating 18 when passing between pole pieces 58 and 60 and pole pieces 12 and 14. Thus, when the tracking control signal is applied to coils 10 and 56, both the fiber 16 and lead wire 20 are deflected in the same direction.

As shown in FIG. 2, it may be desirable to deflect the optical fiber 16 in a second direction indicated by arrows 62 which is perpendicular to the direction 28. For this purpose another electromagnetic transducer means is provided including a coil 64 surrounding a magnetic metal core having pole pieces 66 and 68 on the opposite sides of the optical fiber. However, it should be noted that the coil 64 is connected to another output of the tracking control circuit different than output 52 when employed for tracking purposes. Also, in this embodiment the lead wire 20 should always be connected to a D.C. current source, as shown in FIG. 2.

The optical fiber 16 may be of the self-focusing type described in the Uchida et al article mentioned previously. As shown in FIG. 3, a conical funnel shaped input end 70 may be provided on such fiber for focusing the substantially parallel input light rays 72 to a narrower light beam 74 within the fiber, thereby eliminating the need for the converging lens 34.

As shown in FIGS. 4 and 4A, the optical fiber 16 may be attached to a piezoelectric transducer 76 for deflection of such fiber in response to a control signal applied to the electrodes 78 and 80 on opposite sides of such transducer. Thus, the piezoelectric transducer 76 may be of a bimorph type including a pair of piezoelectric ceramic elements 82 and 84 of different orientation positioned on opposite sides of a center electrode 86 which may be grounded. The side electrodes 78 and 80 are provided on the outer surfaces of the two piezoelectric layers 82 and 84. As a result of the different orientation of the piezoelectric layers, the transducer element 76 bends when a control signal is applied to the side electrodes. This control signal may be provided by the tracking control circuit 48 whose output 52 is connected to electrodes 72 and 78. The piezoelectric transducer 76 is attached along its length to the optical fiber 16 so that such fiber is deflected in the direction of arrows 28 when the piezoelectric elements bend in response to the application of a control signal, as shown in FIG. 4A. It should be noted that the left end of the optical fiber 16 and the left end of the piezoelectric elements are fixed to the support member 36 so that only the right ends of these elements are deflected up and down. Of course in the embodiment of FIG. 4, the conductive coating 18 is not required on the outer surface of the optical fiber and D.C. current source 54 is eliminated.

Another embodiment of the invention using a piezoelectric transducer is shown in FIG. 5 and includes a pair of linear expansion-contraction type piezoelectric elements 88 and 90. These piezoelectric elements 88 and 90 are supported on fixed support arms 92 and 94, respectively, attached to support plate 36. Each of the piezoelectric elements is provided with two electrodes 96 and 98 on opposite sides of the piezoelectric material. Electrodes 96 may be connected to ground and attached to the fixed support arms while the other electrodes 98 are connected to different push-pull output conductors 100 and 102 of the control circuit 48. In addition the electrodes 98 are also physically attached by connecting wires 104 to the optical fiber 16, so that expansion and contraction of the piezoelectric elements causes the fiber to be deflected up and down in the direction of arrows 28. Since the two piezoelectric elements 88 and 90 are connected to push-pull outputs 100 and 102, one of such elements expands while the other one contracts when the control circuit produces push-pull output signals of opposite polarity, thereby causing more efficient deflection of the fiber.

A still further embodiment of the present invention is shown in FIG. 6 and includes a pair of magnetostrictive wires 106 and 108 which are fastened at one end to the optical fiber 16 and are fastened at their other ends to the fixed support plate 36. A pair of electromagnetic coils 110 and 112 are wound about the magnetostrictive wires 106 and 108, respectively. The left end of each of the electromagnetic coils 110 and 112 is grounded while its right end is connected to push-pull outputs 100 and 102 of the tracking control circuit 48. An output signal of one polarity produces a magnetic field about the magnetostrictive wires 106 and 108 such that wire 106 contracts while wire 108 expands. When the polarity of such output signal reverses, the magnetic field is reversed causing wire 108 to contract and wire 106 to expand. As a result, the optical fiber 16 is deflected vertically in the direction of arrows 28. Of course, the wires 106 and 108 should be made of equal length and extend at substantially the same angle with respect to the axis of the fiber 16 on opposite sides thereof to cause equal deflection of the fiber in opposite directions for positive and negative signals of the same amplitude.

In FIG. 7, a thermoelectric transducer is employed for deflection of the optical fibers 16 including a bimetal strip 114 or other thermal expansion element which bends when heated. An electrical heating element 116 is positioned adjacent to the bimetal strip and connected to the output 52 of the control circuit. The bimetal strip 114 is fastened along its length to the optical fiber 116 so that when such strip bends it deflects the optical fiber in the direction of arrows 28 and causes deflection of the light beam 30 transmitted therethrough. It should be noted that this transducer means is much slower in response time than that of the previously discussed transducer means so that it is suitable for only low frequency deflection.

It will be obvious to those having ordinary skill in the art that many changes may be made in the details of the above-described embodiments of the present invention without departing from the spirit of such invention. For example, the optical fiber deflection device can be used as a light pickup device between the record 40 and the photocell 42 to receive light transmitted through or reflected from such record, in which case its input end would be deflected and its output end fixed. Also, the D.C. voltage source 54 can be eliminated and the control signal transmitted through both the coil 10 and the conductor 18 attached to the fiber 16. Therefore, the scope of the present invention should only be determined by the following claims.

I claim:

1. An optical fiber deflection device comprising:
   optical fiber means for transmitting a light beam therethrough;
   electrical transducer means for deflecting at least one end of said fiber means in response to an electrical control signal to deflect said light beam;
   said transducer means including a nonmagnetic deflector means attached to said fiber means for deflection of said fiber means by movement of said deflector means; and
   means for connecting said deflector means to an electrical current source so that said deflector means is moved in response to the application of said control signal to said transducer means.

2. A device in accordance with claim 1 in which the deflector means includes coil means connected to the source of said control signal for producing an electromagnetic field in response to said control signal, said coil means surrounding magnetostrictive elements which are fixed at one end and have their other end attached to the fiber means so that said magnetostrictive elements move axially in response to said electromagnetic field to deflect said fiber means.

3. A device in accordance with claim 1 in which the optical fiber is of the self-focusing type.

4. A device in accordance with claim 1 in which at least one end of the fiber is of a conical shape for focusing the light transmitted through said fiber.

5. A device in accordance with claim 1 in which the transducer means includes piezoelectric means for deflecting the fiber means in response to said control signal.

6. A device in accordance with claim 5 in which the deflector means includes a piezoelectric element attached to said fiber means and connected to the source of the electrical control signal so that said piezoelectric element moves in response to said control signal.

7. A device in accordance with claim 1 in which the deflector means includes a thermal expansion member attached to the fiber means, and an electrical heating element positioned adjacent to said expansion member and connected to the source of said control signal for heating said expansion member to cause it to bend and deflect said fiber means.

8. A device in accordance with claim 7 in which the thermal expansion member is a bimetal strip.

9. A device in accordance with claim 1 in which the transducer means includes an electromagnetic means for deflecting the fiber means in response to the control signal.

10. A device in accordance with claim 9 in which the transducer means includes coil means for producing a magnetic field in response to the transmission of electrical current through said coil means, and the deflector means includes an electrical conductor attached to and extending longitudinally along said fiber means and connected to cause an electrical current to flow through the conductor to produce another magnetic field around said conductor, at least one of said currents being said control signal so that said fiber means is deflected in response to said control signal.

11. A device in accordance with claim 10 in which the other of said currents is a D.C. current.

12. A device in accordance with claim 9 in which the transducer means includes magnet means for producing a fixed magnetic field and the control signal is transmitted through an electrical conductor attached to the fiber means.

13. A device in accordance with claim 12 in which the magnet means is a permanent magnet means.

14. A device in accordance with claim 12 in which the magnet means includes a coil means for producing a fixed magnetic field in response to the transmission of a D.C. current through said coil.

* * * * *